United States Patent [19]

Portnoy

[11] Patent Number: 4,704,122
[45] Date of Patent: Nov. 3, 1987

[54] BI-CONCAVE SMALL INCISION INTRAOCULAR LENS

[75] Inventor: Vladimir Portnoy, Irvine, Calif.

[73] Assignee: American Hospital Supply Corp., Evanston, Ill.

[21] Appl. No.: 728,858

[22] Filed: Apr. 30, 1985

[51] Int. Cl.$^4$ .............................................. A61F 2/16
[52] U.S. Cl. ...................................................... 623/6
[58] Field of Search ...................................... 623/6, 11

[56] References Cited

U.S. PATENT DOCUMENTS

| | | | |
|---|---|---|---|
| 4,074,368 | 2/1978 | Levy, Jr. et al. | 623/6 |
| 4,253,799 | 3/1981 | Banko | 623/6 |
| 4,373,218 | 2/1983 | Schachar | 623/6 |
| 4,402,579 | 9/1983 | Poler | 623/6 X |
| 4,413,359 | 11/1983 | Akiyama et al. | 623/11 |
| 4,424,597 | 1/1984 | Schlegel | 623/6 |

FOREIGN PATENT DOCUMENTS 2114315  8/1983  United Kingdom ..................... 623/6

OTHER PUBLICATIONS

"Silicon Intraocular Lenses in 50 Cataract Cases", *Chinese Medical Journal*, Zhou Kai-yi, Jinniu Hospital, Chengdu, Chinese Medical Association, Mar. 1983, vol. 96, No. 3, pp. 175, 176.

*Primary Examiner*—Ronald L. Frinks
*Attorney, Agent, or Firm*—Gordon L. Peterson

[57] ABSTRACT

An intraocular lens for implantation within the eye comprising an optic having an optical axis, concave anterior and posterior faces and an interior gas-filled chamber. The chamber has concave forward and rear surfaces which extend transverse to the optical axis. A fixation member fixes the optic within the eye. The optic and fixation member are both constructed of a soft, deformable material.

17 Claims, 3 Drawing Figures

BI-CONCAVE SMALL INCISION INTRAOCULAR LENS

BACKGROUND OF THE INVENTION

An intraocular lens, which is commonly referred to as an "IOL", is used to replace the natural lens of the human eye following cataract surgery. To implant an IOL, an incision is made in the eye, and the IOL is inserted through the incision and fixed within the eye in accordance with known techniques. The incision in the eye creates trauma and a possibility of infection. For these and other reasons, it is desirable to minimize the length of the incision.

An IOL commonly includes an optic and fixation means for fixing the optic within the eye. To minimize the size of the incision, both the optic and the fixation means can be made of deformable material so that they can be rolled or deformed for insertion through a relatively small incision. One such IOL is shown in published British Patent Application No. 2,114,315. Although folding or deforming the optic and fixation means for implantation is desirable to reduce the length of the incision, the length of the incision could be further reduced through the use of a foldable optic which employs a lower volume of material.

It is also known to construct an IOL having high magnification by utilizing multiple air lenses in tandem. Each of the air lenses has one or more gas-filled bubbles. One such construction is shown in Levy et al U.S. Pat. No. 4,074,368. The IOL shown in this patent is constructed of rigid material and has a very substantial axial dimension. Accordingly, it is not suited for implantation through a small incision.

SUMMARY OF THE INVENTION

This invention provides a thin IOL which uses a minimum volume of material so that it is easily implantable through a very small incision. The IOL can be constructed of soft, flexible, deformable materials so that it can be folded or deformed for insertion through the incision into the eye. The optic contains a gas which can be compressed when the IOL is folded to reduce the volume of the optic.

The IOL includes an optic body which has anterior and posterior faces and an interior gas-filled chamber. The chamber has forward and rear surfaces which extend generally transverse to the optical axis of the optic.

It is necessary that the optic be a positive lens in that it must focus light on the retina. As explained more fully hereinbelow, the presence of the gas-filled chamber in the optic body requires at least one of the forward and rear surfaces of the chamber be concave. To minimize the material required for the optic body and to enhance thinness of the optic, preferably the forward and rear surfaces and the anterior and posterior faces are concave. However, to the extent that additional material for the optic body can be tolerated, the anterior and posterior faces and one of the forward and rear surfaces need not be concave and may be, for example, planar or convex. However, if one of the forward and rear surfaces is convex, its radius of curvature must be greater than the radius of curvature of the concave surface in order that the optic can function as a positive lens which will focus light on the retina. In this regard, the functional or light-focusing surfaces of the optic body are the forward and rear surfaces rather than the anterior and posterior faces.

The advantage of employing the gas-filled chamber in minimizing the material used for the optic body and in maximizing thinness of the optic can best be understood by considering the basic function of the optic which is to focus the light on the retina. Generally, the ability of an IOL to focus light on the retina is a function of the difference in refractive indices of the optic and the liquid of the eye, e.g., the aqueous humor, and the radii of the forward and rear surfaces of the chamber. If the difference in the refractive indices is increased, the radii can be lengthened, and this results in a thinner optic and a lower volume of material for the optic body.

The refractive index of the aqueous humor is approximately 1.336, and the refractive index for PMMA, which is a commonly used material for the optic, is about 1.491. However, the refractive index for most applicable gases is essentially 1.0. By utilizing a gas-filled chamber, the difference in the refractive indices is approximately doubled as compared to PMMA. Accordingly, the radii of the forward and rear surfaces of the chamber can be lengthened to thereby reduce the thickness of the optic compared to a conventional optic.

Only one of the gas-filled chambers is required. This further minimizes the thickness of the optic.

Because the walls of the optic are thin, additional strength can be imparted to them if they are joined together at central regions of the walls. This makes the chamber of generally annular configuration.

The forward and rear surfaces of the chamber may be defined by a very thin coating. The coating reduces the migration of gas out of the chamber through the walls of the optic.

The optic and fixation means are both preferably constructed of a soft, deformable material, such as silicone. This enables the IOL to be folded or deformed to facilitate implantation through a small incision. The fixation means preferably surrounds the optic and serves as a frame to help support the flexible optic.

A soft, deformable optic having a gas-filled chamber can be used to adjust or vary the diopter power of the IOL. This can be accomplished by placing a quantity of gas in the chamber to control the spacing between, and/or curvature of, the forward and rear surfaces. By controlling the spacing between, and/or curvature of, these surfaces, the diopter power of the IOL can be adjusted the desired amount. This feature of the invention does not require that the forward or rear surfaces be concave but only that they be movable or curvable so that the spacing or curvature thereof can be varied with the gas pressure in the chamber. If this feature is employed, the central regions of the walls of the optic are preferably resiliently joined together or left unjoined.

The placing of the desired quantity of gas in the chamber to adjust the diopter power can be carried out in various ways, such as by inflating the chamber to provide the desired quantity of gas or over-inflating the chamber and thereafter deflating the chamber to provide the desired quantity of gas. The desired quantity of gas can be placed into the chamber before and/or after implantation of the IOL. The usual ambient pressure or temperature changes are not sufficient to meaningfully alter the diopter power.

The invention, together with additional features and advantages thereof, may best be understood by reference to the following description taken in connection with the accompanying illustrative drawing.

DESCRIPTION OF THE PREFERRED EMBODIMENT

Figure 1:
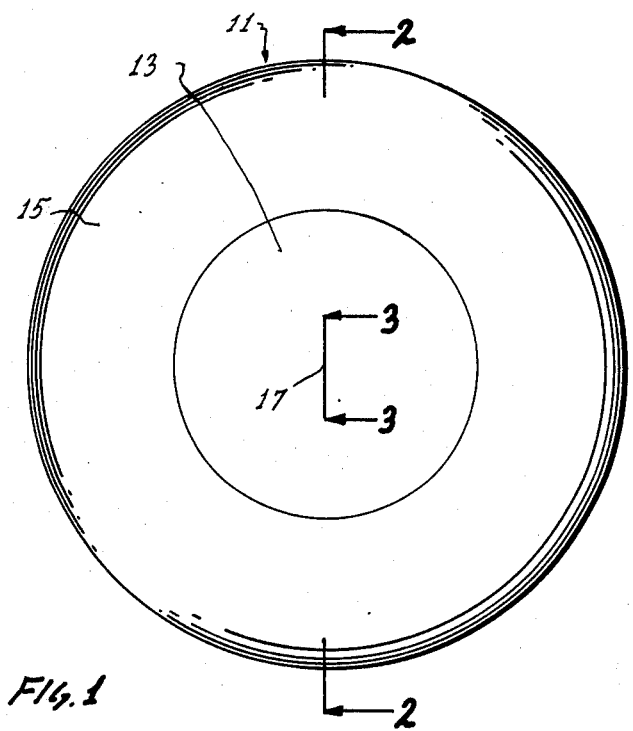
FIG. 1 is a front elevational view of an IOL constructed in accordance with the teachings of this invention.

FIG. 1 shows an IOL 11 which includes an optic 13 of circular configuration and fixation means in the form of an annular fixation member 15 integral with, and surrounding, the optic 13. The optic has an optical axis 17 and includes an envelope or optic body 18. Although various different constructions are possible, in the illustrated embodiment, the optic body 18 and the fixation member 15 are integrally constructed of a soft, flexible, deformable material, such as silicone, so that the IOL 11 can be folded for insertion through a small incision in the eye.

The optic body 18 has a concave anterior face 19, a concave posterior face 21 and an interior chamber 23. The optic 13 includes, in addition to the optic body 18, a gas in the chamber 23 which forms a gas lens, which in the illustrated embodiment, is biconcave. The chamber 23 has a concave forward surface 25 and a concave rear surface 27 which, like the anterior face 19 and posterior face 21, extend generally transverse to the optical axis 17. The optic body 18 has an anterior wall 29 between the anterior face 19 and the forward surface 25 and a posterior wall 31 between the posterior face 21 and the rear surface 27. The walls 29 and 31, which may be of uniform thickness, are preferably very thin and may be, for example, 0.05 millimeter or less in thickness.

To strengthen the optic 13, radially short central regions 33 of the walls 29 and 31 at and near the optical axis 17 can be joined together resiliently in any suitable manner, such as by bonding. With the central regions 33 joined together, the chamber 23 is annular. The chamber 23 has a cylindrical periphery 35 of very short axial dimension.

All of the surfaces of the chamber 23, i.e., the forward surface 25, the rear surface 27 and the cylindrical periphery 35, are each defined by, or coated with, a coating which resists the migration of the gas through the silicone. The coating, which may be, for example, a carbonate coating, is extremely thin and may be of the order of 2 to 4 millionths of an inch in thickness.

The radii of the surfaces 25 and 27 will vary with the diopter power, but in any event, will be relatively long. For example, for a diopter power of 20, the radius of the forward surface 25 and of the rear surface 27 may be, for example, 33.4 millimeters. Preferably, the anterior face 19 and the posterior face 21 each have the same radius as the surfaces 25 and 27. The optic 13 may also be extremely thin and may be, for example, twice the thickness of either of the walls 19 and 21 at the optical axis 17. The overall thickness of the optic 13 at the periphery 35 may be, for example, about 0.26 millimeter for a 6 millimeter diameter optic.

The chamber 23 is filled with a suitable gas. The gas should be inert so as not to harm, or react with, other portions of the IOL 11 or harm the eye if it should escape. Preferably, the gas is heavy to reduce the tendency of it to escape. Argon is one example of a suitable gas.

The pressure within the chamber 23 can be changed to vary the spacing between, and the curvature of, the surfaces 25 and 27 to change the diopter power of the optic 13. Gas can be injected into the chamber 23 or removed from it by, for example, a needle which can be forced through either of the walls 29 and 31 into the chamber 23. In the embodiment illustrated, the primary effect of this is to change the curvature of the surfaces 25 and 27. Of course, the puncture hole must be sealed following removal of the needle.

Figure 2:
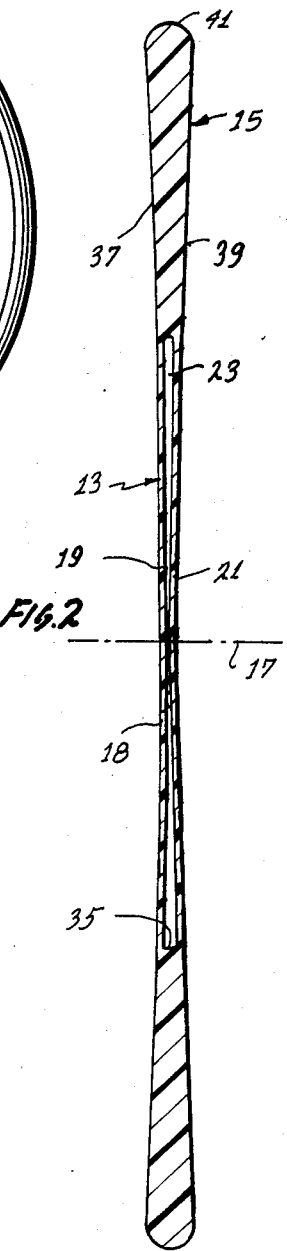
FIG. 2 is an enlarged sectional view taken generally along line 2—2 of FIG. 1.
Figure 3:
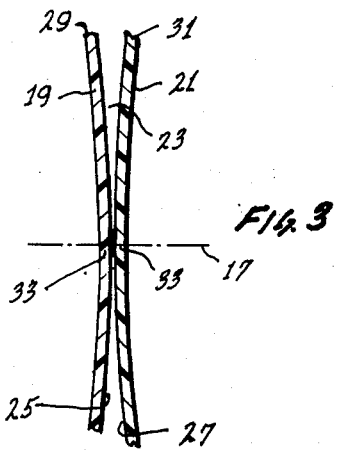
FIG. 3 is an enlarged fragmentary sectional view taken generally along line 3—3 of FIG. 1.

Unlike conventional IOL's, the fixation member 15 is less flexible than the optic 13 in that it is much thicker than the walls 29 and 31 and serves as a frame to help support the optic. Although the size and configuration of the fixation member 15 can be varied as desired, preferably the fixation member surrounds the optic. As shown in FIG. 2, the anterior face 19 and the posterior face 21 are extended radially to form an anterior face 37 and a posterior face 39, respectively, of the fixation member 15. The faces 37 and 39 are concave and have the same radius as the faces 19 and 21, but this is not required. The fixation member 15 has a smoothly curved peripheral surface 41. The IOL 11 uses only a very small amount of material and is very lightweight. To further reduce the material used for the IOL 11 and make it even lighter and rollable or foldable into a smaller configuration for insertion through an incision, the fixation member 15 can be scalloped or have various other portions of it removed.

The IOL 11 can be rolled or folded into an extremely small package for insertion through a very small incision into the eye. The gas in the chamber can be compressed when the IOL is folded to reduce the volume of the gas and of the optic 13 for insertion through the incision. For example, the IOL 11 could be injected through a needle into the posterior chamber of the eye, and the needle may have a very small diameter. The IOL 11 is sufficiently resilient so that it tends to return to the unrestrained position of FIGS. 1 and 2 following implantation. Following implantation, a quantity of the gas in the chamber 23 can be increased or reduced using the needle technique described above to change the diopter power of the IOL.

The IOL 11 can be made using conventional techniques. For example, the optic body 18, which includes the walls 29 and 31 and a very thin annular layer that includes the cylindrical periphery 35, may be cast in a membrane casting operation about a plug. Next, the fixation member 15 is cast around the optic body 18 to make the fixation member integral with the optic body. The plug is dissolved by injecting a suitable solvent through a needle into the plug, and the resulting solution is also removed with a needle. The chamber 23 is then filled with gas using a second needle, and the puncture hole from the needle is sealed after this second needle is removed. If it is desired to provide the internal coating on the surfaces of the chamber 23, this coating is previously deposited on the plug so that it will adhere to the surfaces of the chamber 23 following the membrane-casting step.

Although an exemplary embodiment of the invention has been shown and described, many changes, modifications and substitutions may be made by one having ordinary skill in the art without necessarily departing from the spirit and scope of this invention.

I claim:

1. An intraocular lens for implantation within the eye comprising:

an optic having an optical axis and including an optic body of deformable material, said optic body having anterior and posterior faces and an interior chamber, said chamber having a gas therein forming a gas lens and forward and rear surfaces which extend generally transverse to the optical axis, at least one of said surfaces of the chamber being concave, said optic when implanted being adapted to focus light on the retina;

fixation means for fixing the optic within the eye; and said optic having an anterior wall between the anterior face and the forward surface and a posterior wall between the posterior face and the rear surface and said intraocular lens including means for joining central regions of said walls together.

2. An intraocular lens as defined in claim 1 wherein both of said surfaces of said chamber are concave whereby the gas lens is bi-concave.

3. An intraocular lens as defined in claim 1 wherein said faces are concave.

4. An intraocular lens as defined in claim 1 wherein said chamber is the only chamber within the optic.

5. An intraocular lens as defined in claim 1 wherein said chamber is generally annular.

6. An intraocular lens as defined in claim 1 including a coating defining said surfaces, said coating reducing gas transmission out of the chamber.

7. An intraocular lens as defined in claim 1 wherein both of said surfaces of said chamber are concave and said fixation means is constructed of a soft deformable material integral with the optic.

8. An intraocular lens as defined in claim 7 wherein said optic has an anterior wall between the anterior face and the forward surface and said wall has a thickness of no more than about 0.05 mm.

9. An intraocular lens as defined in claim 7 wherein both of said faces are concave.

10. An intraocular lens as defined in claim 1 wherein said fixation means serves as a frame for the optic.

11. An intraocular lens as defined in claim 10 wherein the optic and fixation means are flexible, said optic being more flexible than the fixation means.

12. An intraocular lens for implantation within the eye comprising:

an optic having an optical axis, anterior and posterior faces and an interior gas-filled chamber, said chamber having forward and rear surfaces which extend generally transverse to the optical axis, at least one of said surfaces being concave and said optic when implanted being adapted to focus light on the retina;

fixation means for fixing the optic in the eye;

said optic having an anterior wall between the anterior face and the forward surface and a posterior wall between the posterior face and the rear surface; and means for joining central regions of said walls together.

13. An intraocular lens as defined in claim 12 including a coating defining said surfaces, said coating reducing gas transmission out of the chamber.

14. An intraocular lens as defined in claim 12 wherein both of said surfaces of said chamber are concave.

15. An intraocular lens as defined in claim 12 wherein said faces are concave.

16. An intraocular lens as defined in claim 12 wherein said chamber is the only chamber within the optic.

17. An intraocular lens as defined in claim 12 wherein both of the faces and surfaces are concave.

* * * * *